(12) United States Patent
Kalinin et al.

(10) Patent No.: US 7,897,777 B2
(45) Date of Patent: Mar. 1, 2011

(54) PROCESS OF ENANTIOMERIC RESOLUTION OF D,L-(±)-THREO-METHYLPHENIDATE

(75) Inventors: Alexei Kalinin, Springfield, MO (US); Guofang Qiu, Springfield, MO (US); Thomas J. Marren, Springfield, MO (US); James E. Aldred, Jr., Springfield, MO (US); Yu Ji, Springfield, MO (US)

(73) Assignee: Archimica, Inc., Springfield, MO (US)

( * ) Notice: Subject to any disclaimer, the term of this patent is extended or adjusted under 35 U.S.C. 154(b) by 1000 days.

(21) Appl. No.: 11/650,278

(22) Filed: Jan. 5, 2007

(65) Prior Publication Data

US 2008/0167470 A1    Jul. 10, 2008

(51) Int. Cl.
*C07D 211/34* (2006.01)
(52) U.S. Cl. ..................................... 546/233
(58) Field of Classification Search .................. 546/233
See application file for complete search history.

(56) References Cited

U.S. PATENT DOCUMENTS

| | | | | |
|---|---|---|---|---|
| 6,096,760 | A | 8/2000 | Sapino | 514/317 |
| 6,100,401 | A | 8/2000 | Prashad et al. | 546/233 |
| 6,162,919 | A | 12/2000 | Prashad et al. | 546/233 |
| 6,242,464 | B1 | 6/2001 | Harris et al. | 514/317 |
| 6,531,489 | B2 | 3/2003 | Harris et al. | 514/317 |
| 7,164,025 | B2 | 1/2007 | Langston et al. | 546/240 |
| 7,229,557 | B2 * | 6/2007 | Krsek et al. | 210/656 |
| 2005/0171155 | A1 | 8/2005 | Krsek et al. | 514/317 |
| 2005/0277667 | A1 | 12/2005 | Kumar et al. | 514/317 |

FOREIGN PATENT DOCUMENTS

| | | |
|---|---|---|
| WO | WO 97/27176 A1 | 7/1997 |
| WO | WO 98/25902 A1 | 6/1998 |
| WO | WO 03/031411 A2 | 4/2003 |
| WO | WO 2004/069799 A1 | 8/2004 |

OTHER PUBLICATIONS

Prashad, Mahavir, "Approaches to the Preparation of Enantiomerically Pure (2R,2'R)-(+)-*threo*-Methylphenidate Hydrochloride" Review, (2001) pp. 379-392.

Prashad, Mahavir, "Resolution of (±)-threo-Methylphenidate with (R)-(−)-Binaphthyl-2,2"-Diyl Hydrogen Phosphaate: 0.5 M Equiv of Resolving Agent Is Better than 1M Equiv" Review, (2001) pp. 379-392.

Prashad, Mahavir et al., "An efficient large scale resolution of (±)-*threo*-methylphenidate hydrochloride (Ritalin® Hydrochloride)" Tetrahedron: Asymmetry 10, (1999) pp. 3111-3116.

* cited by examiner

*Primary Examiner*—Celia Chang
(74) *Attorney, Agent, or Firm*—ProPat, L.L.C.

(57) ABSTRACT

A process for preparing the d-threo isomer of methylphenidate hydrochloride which includes (i) resolving a racemic mixture of racemic threo-methylphenidate hydrochloride with a less than stoichiometric amount of tertiary amine base to obtain a methylphenidate-chiral acid salt, (ii) basifying the methylphenidate-chiral acid salt to obtain methylphenidate free base, and (iii) converting the methylphenidate free base into d-threo-methylphenidate hydrochloride.

28 Claims, No Drawings

PROCESS OF ENANTIOMERIC RESOLUTION OF D,L-(±)-THREO-METHYLPHENIDATE

FIELD OF THE INVENTION

The present invention relates to chiral resolution processes and, more particularly, relates to improved processes for preparing either the d or l-threo isomer of methylphenidate hydrochloride using a chiral acid.

BACKGROUND OF THE INVENTION

Racemic threo-methylphenidate hydrochloride is an amphetamine-like prescription stimulant which is marketed for the treatment of Attention Deficit Hyperactivity Disorder in children and adults. Studies of racemic threo-methylphenidate have indicated that the d-threo-enantiomer is much more active than the corresponding l-threo-enantiomer. Furthermore, the l-threo-methylphenidate enantiomer has been postulated to impart side effects and euphoric effects.

Several methods have been disclosed in the literature for preparing the d-threo enantiomer of methylphenidate hydrochloride.

Methods for resolving threo methylphenidate into its enantiomers involve using 1,1'-binaphthyl-2,2'-diyl hydrogen phosphate as a resolving agent have been proposed. Methods employing expensive 1,1'-binaphthyl-2,2'-diyl hydrogen phosphate as a resolving agent are disclosed in Patrick et al (The Journal of Pharmacology and Experimental Therapeutics, 241:152-158 (1987)) and U.S. Pat. No. 6,162,919.

Several methods for resolving threo-methylphenidate free base have also been disclosed. Resolution of threo-methylphenidate is taught in U.S. Pat. No. 6,121,453 and 6,242,464, for example. The preparation and isolation of the threo-methylphenidate free base prior to resolution makes large scale preparation cumbersome.

Resolutions of threo-methylphenidate hydrochloride using aroyltartaric acids are described in U.S. Pat. No. 6,100,401 and Tetrahedron (Asymmetry) 10: 311-3116 (1999). These resolutions take place in aqueous methanol with threo-methylphenidate hydrochloride, di-p-isopropylbenzoyl- and benzoyl-D-tartaric acids and N-methylmorpholine taken in equimolar amounts.

Methods involving resolution of amide derivatives, followed by hydrolysis and esterification are also known, as described in U.S. Pat. No. 2,957,880 and Published U.S. application No. 2006/135777.

Two step resolutions are known in the art as well. Such methods involve two separate resolution steps utilizing two different resolution agents, as disclosed in Published U.S. application No. 2005/171155. Such two step resolutions are problematic in that they slow productivity and thus increase cost.

Accordingly, there remains a need in the art for a more practical, robust and economic process for preparing the d-threo isomer of methylphenidate hydrochloride.

SUMMARY OF ADVANTAGEOUS EMBODIMENTS OF THE INVENTION

Surprisingly, Applicants have found that, rather than rely on expensive raw materials and/or additional process steps, the use of tailored stoichiometry within the resolution step provides dexmethylphenidate of high enantiomeric purity and in high yields.

The inventive processes generally isolate either d- or l-threo-isomer of methylphenidate hydrochloride by initially resolving a mixture including racemic threo-methylphenidate hydrochloride; less than or equal to about 1.0 equivalent (based on the amount of racemic threo-methylphenidate) of chiral acid selected from one or more di-0-0'-aroyl tartaric acids, and less than 1.0 equivalent (based on the amount of racemic threo-methylphenidate) of one or more tertiary amine bases in a solvent mixture comprising one or more lower alkanols and water to form a diastereomerically enriched salt of chiral acid with the desired isomer of threo-methylphenidate.

The chiral acid-isomeric methylphenidate salt is then basified to obtain isomeric methylphenidate free base, and the isomeric methylphenidate free base is subsequently converted into isomeric methylphenidate hydrochloride having an enantiomeric excess of greater than about 95%.

Further objects, features and advantages of the present invention will become apparent from the detailed description of preferred embodiments which follows.

DETAILED DESCRIPTION OF ADVANTAGEOUS EMBODIMENTS OF THE INVENTION

The present invention provides an improved process for preparing the d-threo isomer of methylphenidate hydrochloride directly from a racemic mixture of threo-methylphenidate hydrochloride by processes which generally comprise (I) chiral resolution of d,l-threo-methylphenidate hydrochloride into a d-threo-methylphenidate/chiral acid salt; (II) basification of the d-threo-methylphenidate/chiral acid salt to form d-threo-methylphenidate free base and (III) conversion of the d-threo-methylphenidate free base into d-threo methylphenidate hydrochloride.

The process steps (I) through (III) are illustrated below:

Step I: Chiral Resolution:

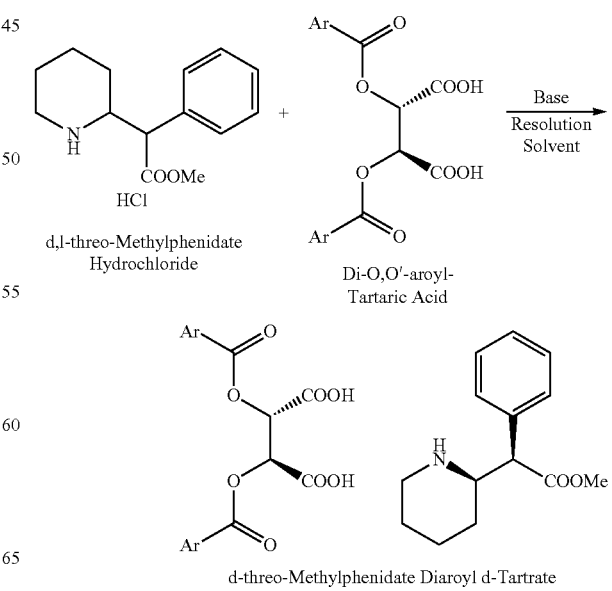

Step II: Free Base Generation via Basification:

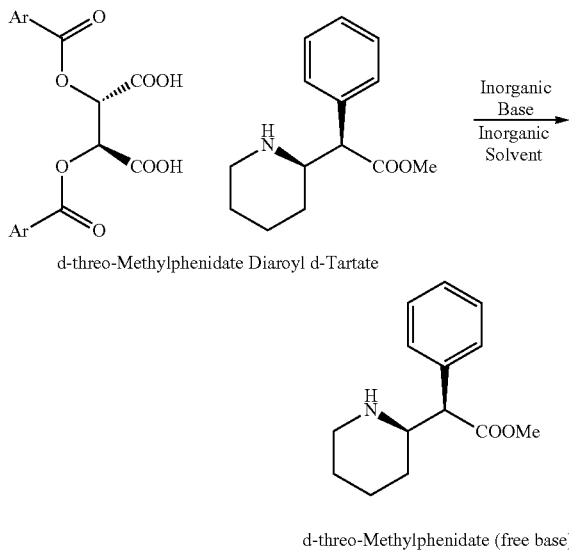

d-threo-Methylphenidate Diaroyl d-Tartate d-threo-Methylphenidate (free base)

Step III: Hydrochloride Salt Formation:

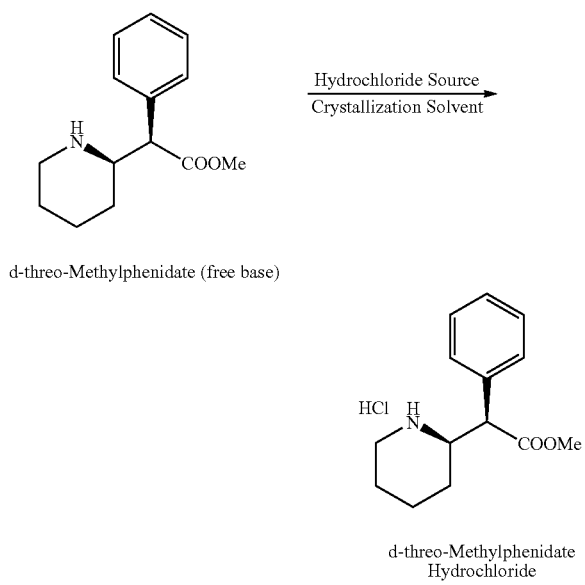

d-threo-Methylphenidate (free base)

d-threo-Methylphenidate Hydrochloride

During the chiral resolution racemic threo-methylphenidate hydrochloride forms a salt with one or more chiral acids in the presence of one or more bases and a resolution solvent, thereby forming a d-threo-methylphenidate/chiral acid salt which advantageously precipitates. As noted above, the present invention is directed to the use of beneficial stoichiometric amounts within the resolution step to provide a heretofore unknown balance of high enantiomeric excess ("ee") and yield of d-threo-methylphenidate hydrochloride.

Suitable chiral acids include any optically enriched chiral acid capable of forming an isolable salt with racemic methylphenidate. In advantageous embodiments, di-0,0'-aroyl-D- or L-tartaric acid can be used as a chiral acid to resolve racemic threo-methylphenidate. Non-limiting exemplary di-0,0'-aroyl-tartaric acids include one or more of di-p-toluoyl-D-tartaric acid, di-m-toluoyl-D-tartaric acid and di-benzoyl-D-tartaric acid. In advantageous embodiments the chiral acid is di-p-toluoyl-D-tartaric acid.

The chiral acid may generally be present in amounts ranging from about 0.4 to 1.1 equivalent, based on the amount of the racemic threo-methylphenidate hydrochloride "bormp", such as amounts ranging from about 0.5 to 1.1 equivalent, bormp, particularly amounts ranging from about 0.60 to 1.0 equivalent, bormp.

Suitable bases include any base, either organic or inorganic, which forms a dissolvable salt with the chiral acid within the resolution media and which further allows the subsequent release of the d-threo-methylphenidate free base from its hydrochloride form. Non-limiting exemplary bases include tertiary amines and alkali metal bases. Suitable tertiary amines include N-methylmorpholine (also referred to as 4-methylmorpholine), triethylamine and diisopropylethylamine, and mixtures thereof. Suitable alkali metal bases include sodium hydroxide and sodium acetate. In advantageous embodiments, the base is a tertiary amine, particularly N-methylmorpholine.

Surprisingly, the instant invention has found that the type and amount of base used within the resolution step strongly affects the resulting yield and enantiomeric excess ("ee").

For alkali metal bases, d-threo-methylphenidate/chiral acid salt yields generally improve as the amount of chiral acid and/or alkali metal base comes closer or equal to their respective stoichiometric ratio, based on the amount of racemic threo-methylphenidate hydrochloride. For example, alkali metal base embodiments provide higher d-threo-methylphenidate/chiral acid salt yields when incorporating one equivalent of alkali metal base and one equivalent of chiral acid. The enantiomeric excess ("ee") for alkali metal base embodiments is quite elevated, i.e. about 95% and above, for both low stoichiometric and equal amounts of chiral acid and/or alkali metal base.

Accordingly, the inventive resolution step may advantageously include alkali metal bases in amounts ranging from about 0.8 up to 1.2 equivalent, bormp, such as amounts ranging from about 0.9 to 1.1 equivalent, bormp.

In sharp contrast, the presence of tertiary amine base in less than stoichiometric amounts relative to the racemic threo-methylphenidate hydrochloride provides a highly advantageous balance of yield and ee for the d-threo-methylphenidate/chiral acid salt. For example, incorporation of tertiary amine in less than stoichiometric amounts (bormp) provides d-threo-methylphenidate/chiral acid salt yields of greater than about 35%, such as about 40% (50% yield being maximum) and an ee of about 95% and above for the d-threo-methylphenidate/chiral acid salt. Surprisingly, under the same reaction conditions incorporation of tertiary amine at its stoichiometric amount (bormp) provided far lower ee's for the d-threo-methylphenidate/chiral acid salt.

Accordingly, the inventive resolution step may advantageously include tertiary amine base in amounts ranging from about 0.4 to less than 1.0 equivalent, bormp. In particularly advantageous embodiments, the inventive resolution step may include tertiary amine base in amounts ranging from about 0.50 to about 0.75 equivalent, bormp, such as from about 0.55 to about 0.60 equivalent, bormp.

Applicants further determined that the use of tertiary amine base in less than stoichiometric amounts (bormp) allowed the incorporation of less than stoichiometric amounts (bormp) of chiral acid, without significant detriment to either the yield or ee of the d-threo-methylphenidate/chiral acid salt. For example, incorporation of both tertiary amine and chiral acid in less than stoichiometric amounts (bormp) likewise provides d-threo-methylphenidate/chiral acid salt yields of greater than about 35%, such as about 40% (50% yield being maximum) and an ee of about 95% and above. The advantages imparted by the incorporation of less than stoichiometric amounts of both chiral acid and tertiary amine base was altogether surprising and highly beneficial.

For inventive processes incorporating tertiary amine base, the chiral acid may advantageously be present in the chiral resolution step (I) in amounts ranging from about 0.40 to less than or equal to 1.0 equivalent, bormp, such as amounts ranging from about 0.55 to 0.75 equivalent, bormp. In especially inventive processes incorporating tertiary amine base, the chiral acid may be present in the resolution step (I) in amounts ranging from about 0.50 to 0.60 equivalent, bormp.

The resolution solvent may be any solvent (or solvent mixture) in which the racemic methylphenidate and chiral acid are soluble, either completely or partially. Non-limiting exemplary resolution solvents include one or more lower alkanols and water. Suitable lower alkanols include methanol, ethanol and the like. In advantageous embodiments, the resolution solvent comprises a mixture of lower alkanol and water, particularly methanol and water.

In general, material recovery in the chiral resolution is favored by smaller lower alkanol to water ratios. Exemplary resolution solvent weight ratios of lower alkanol to water range from about 1.4:1 to 2.5:1, such as a resolution solvent ratio of about 1.5:1 to 2.0:1.

The chiral resolution is conducted within an effective amount of a resolution solvent. Higher ee's are generally favored as the chiral resolution becomes more dilute, however, i.e. the lower alkanol to racemic threo-methylphenidate ratio increases. Exemplary weight ratios for lower alkanol to racemic methylphenidate range from about 2.5 to 3.5, such as from about 2.6 to 3.0.

The racemic threo-methylphenidate, chiral acid and base may be introduced into the chiral resolution in any order. The racemic methylphenidate, chiral acid and base may further be introduced independently of one another. Alternatively, the base and chiral acid may be introduced to the chiral resolution as a pre-formed salt.

The chiral resolution generally proceeds by initially charging the racemic threo-methylphenidate, chiral acid and lower alkanol to a suitable reactor under agitation and ambient conditions. The base is then charged at a temperature ranging from about 20 to 30° C., and the resulting slurry is heated to an effective temperature, such as about 40 to 55° C. Process water is then charged and the mixture may be aged, such as aging at 40 to 45° C. for an effective amount of time, such as from about 15 minute to 1 hour. The heated resolution mixture is then cooled to a temperature and for a time effective to precipitate the d-threo-methylphenidate chiral acid salt. For example, the reaction can be cooled to about 0 to 25° C. over the course of approximately 1 to 3 hours and then aged at about 0 to 25° C. for about 1 to 3 hours. The precipitated d-threo methylphenidate/chiral acid salt is then isolated, such as by filtration.

The chiral resolution step may optionally comprise a seeding step, in which the preformed seeds of chiral acid-isomeric methylphenidate salt are introduced to the resolution mixture to affect crystallization of the desired (same isomer as the seed) chiral acid-isomeric methylphenidate salt.

Surprisingly, to achieve high enantiomeric excess crystallization-inducing seeding is not required within the inventive chiral resolution. This avoidance of seeding is highly beneficial, as it further minimizes the unit operations required to manufacture the final product. This lack of seeding further evidences the robust nature of the inventive chiral resolution.

The yield for the dried d-threo-methylphenidate/chiral acid salt is typically above about 35%, such as from about 40 to 44% (50% is theoretical yield). The dried d-threo methylphenidate/chiral acid salt further generally exhibits and ee of greater than 90%, such as an ee of greater than 95%. In particularly advantageous embodiments, the dried d-threo-methylphenidate/chiral acid salt exhibits and ee of greater than 97%, and most preferably an ee of greater than 99%.

The free base generation step, also referred to as basification, (Step II) generally involves the basification of the desired threo-methylphenidate/chiral acid salt obtained in Step I with an inorganic base in the presence of organic solvent to form the free base form of the desired threo-methylphenidate enantiomer.

The inorganic base is advantageously an aqueous alkali metal hydroxide solution, such as a sodium hydroxide solution.

The basification step solvent may be any organic solvent having limited solubility in water. Non-limiting exemplary solvents include esters of acetic acid, such as one or more of ethyl acetate or isopropyl acetate. The role of the solvent is to facilitate separation of threo-methylphenidate free base from the reaction media by extraction.

Basification generally proceeds by initially slurrying the d-threo methylphenidate/chiral acid salt in the basification solvent and subsequently introducing the inorganic base, followed by d-threo methylphenidate free base isolation. The basification and d-threo methylphenidate free base isolation may be carried out under conditions that are generally known to those skilled in the art.

Hydrochloride salt formation (Step III) converts the enantiomerically enriched d-threo-methylphenidate free base obtained from the free base generation Step II to the corresponding hydrochloride salt of equal or higher enantiomeric purity, followed by isolation of the resulting d-threo-methylphenidate hydrochloride.

The conversion generally proceeds by diluting the d-threo-methylphenidate free base in a conversion solvent. Suitable conversion solvents include any solvent in which dexmethylphenidate hydrochloride crystallizes. Non-limiting exemplary conversion solvents include esters of acetic acid, alcohols and water. Suitable non-limiting esters of acetic acid include ethyl acetate and isopropyl acetate. Suitable non-limiting alcohols include methanol, ethanol and isopropanol. In advantageous embodiments, the conversion solvent is a mixture of isopropanol (IPA) and methanol (MeOH). In beneficial aspects of such advantageous embodiments, the conversion solvent includes MeOH in excess of IPA. For example, the conversion solvent may beneficially have an an IPA to MeOH weight ratio ranging from about 1:1 to 10:1, such as about 5:1 ratio of IPA to MeOH.

Suitable non-limiting hydrochloride sources include aqueous or gaseous hydrochloride, hydrochloric acid, acetyl chloride and thionyl chloride. In particularly advantageous embodiments, hydrochloric acid is used as the hydrochloride source.

Hydrochloride salt formation generally proceeds by combining d-threo-methylphenidate free base and at least an equivalent amount of a hydrochloride source within the conversion solvent. The resulting dexmethylphenidate hydrochloride ("DexHCl") is crystallized, isolated and dried. The hydrochloride salt formation, crystallization, isolation and drying steps may be carried out under conditions that are generally known to those skilled in the art.

Although not required, the ee of the DexHCl wet cake may optionally be upgraded by reslurrying in an effective amount of an upgrade solvent. Advantageously, the upgrade solvent is a mixture of methanol (MeOH) and isopropyl alcohol (IPA), particularly a mixture which includes an excess of MeOH relative to IPA, such as about a 3:1 MeOH to IPA weight ratio.

The foregoing process steps generally result in dexmethylphenidate hydrochloride having extremely high enantiomeric purities and good yields. The dexmethylphenidate hydrochloride produced typically has an ee of greater than 90%, more advantageously greater than 97%, and most advantageously greater than 99%. The dexmethylphenidate hydrochloride produced typically has a yield of greater than about 30% based on racemic threo-methylphenidate hydrochloride (50% is max. theoretical yield), more advantageously a yield of greater than about 35%, and most advantageously a yield of about 40%.

Either isomer of methylphenidate can be obtained using the foregoing methods, e.g. by using the D- or L-isomer of the chiral acid as required.

Racemic methylphenidate hydrochloride generally includes a mixture of two diastereomers, threo and erythro, each of which is also a mixture of the corresponding enantiomers. Although the invention is illustrated using racemic threo-methylphenidate hydrochloride as a starting raw material, racemic methylphenidate could theoretically be used as the starting material, as well.

As used herein, racemates or racemic mixtures refers to any mixture of enantiomers and/or diastereomers present in any ratio.

As used herein the d-threo enantiomer of methylphenidate may alternatively be referred to as (2R,2R')-threo-methylphenidate or dexmethylphenidate.

As used herein and in the following claims, articles such as "the", "a" and "an" can connote the singular or plural.

As used herein, all process steps are conducted at atmospheric pressure and ambient temperature, unless indicated otherwise.

The invention is illustrated below with reference to non-limiting inventive and comparative examples. As used herein, percentages are based on weight, unless specified otherwise or obvious from the context.

The enantiomeric excess of all chiral materials described herein may be determined using high pressure liquid chromatography under conditions that are generally known to those skilled in the art.

EXAMPLES

Examples 1 and 2 and Comparative Examples 1 and 2

Effect of Tertiary Amine Base and Resolving Agent Equivalents on Yield and Enantiomeric Purity of D-threo-Methylphenidate/Chiral Acid Salt Threo-methylphenidate hydrochloride (10.0 g, 0.037 mol) was suspended in methanol (36 g) and di-p-toluoyl-d-tartaric acid (D-TA) was charged (see Table 1 for charge quantities) and the formed mixture was heated to 45° C. to provide a clear solution. The mixture was treated with diisopropylethylamine (DIPEA, see Table 1 for charge quantities) while an internal temperature below 45° C. was maintained. Deionized water was added to the mixture at about 45° C. until a cloudy point was achieved. The resulting slurry was cooled to 20° C. over 1 hour, aged for 2 hours, cooled to 0° C. and aged for 1 hour. The formed precipitate of D-threo-Methylphenidate/Chiral Acid Salt (Dex-TA) was filtered and washed sequentially with 20 ml of cold (0-5° C.) MeOH/water (2:1 w/w) mixture, 40 ml of deionized water and 40 ml acetone. The Dex-TA wet cake was dried at 50° C. in vacuum overnight. A reference sample of Dex-TA exhibits mp 161.8° C. and $\alpha^{25}_D$ +121.8° (c 1 wt %, MeOH).

TABLE 1

| | D-TA | | DIPEA | | | Dex-TA | | |
|---|---|---|---|---|---|---|---|---|
| | Equiv | g | Equiv | g | Water g | g | Yield, % | EE, % |
| Ex 1 | 0.5 | 7.2 | 0.5 | 2.4 | 25 | 9.3 | 40.4 | 99.2 |
| C Ex 1 | 0.5 | 7.2 | 1.0 | 4.8 | 123 | n/a* | n/a | n/a |
| Ex 2 | 1.0 | 14.3 | 0.5 | 2.4 | 24 | 9.2 | 40.0 | 99.5 |
| C Ex 2 | 1.0 | 14.3 | 1.0 | 4.8 | 21 | 16.0 | 69.5 | 45.5 |

*No crystallization took place

Altogether unexpectedly, resolution recipes utilizing 0.5 equivalents of DIPEA and 0.5 to 1.0 equivalent of D-TA provided Dex-TA of high chiral purity with about a 40% yield (50% is theoretical yield). Furthermore, increasing the amount of DIPEA to 1.0 equivalents actually had an undesirable effect on yield and ee. For example, a 1:2 ratio of D-TA to DIPEA resulted in no crystallization at all, as illustrated in C Ex 1.

Examples 3 Through 8

Effect of Various Tertiary Amine Bases on Yield and Enantiomeric Purity of D-threo-Methylphenidate/Chiral Acid Salt The procedure of Example 1 was repeated, except that different amounts of and/or differing tertiary amines were substituted for the DIPEA (charged tertiary amine and associated charge amounts are shown in Table 2).

TABLE 2

| | D-TA | | DIPEA | | TEA | | NMM | | Dex-TA | | |
|---|---|---|---|---|---|---|---|---|---|---|---|
| | Equiv | g | Equiv | g | Equiv | g | Equiv | g | g | Yield % | EE % |
| Ex 3 | 0.55 | 7.9 | 0.55 | 2.6 | | | | | 9.5 | 41.3 | 99.8 |
| Ex 4 | 0.70 | 10.0 | 0.55 | 2.6 | | | | | 9.5 | 41.3 | 99.9 |
| Ex 5 | 0.55 | 7.9 | | | 0.50 | 1.9 | | | 9.2 | 40.0 | 99.9 |
| Ex 6 | 0.55 | 7.9 | | | 0.55 | 2.1 | | | 9.4 | 40.9 | 99.9 |
| Ex 7 | 0.55 | 7.9 | | | | | 0.55 | 2.1 | 9.8 | 42.7 | 99.5 |

TABLE 2-continued

|  | D-TA | | DIPEA | | TEA | | NMM | | Dex-TA | | |
| --- | --- | --- | --- | --- | --- | --- | --- | --- | --- | --- | --- |
|  | Equiv | g | Equiv | g | Equiv | g | Equiv | g | g | Yield % | EE % |
| Ex 8 | 0.55 | 7.9 | | | | | 0.55 | 2.1 | 9.4 | 40.9 | 99.6 |

The foregoing resolution processes further illustrate the advantageous incorporation of tertiary amine base allowing the beneficial use of less than an equivalent amounts of base and/or chiral acid without significant sacrifice to ee and yield.

Examples 9 through 12

Effect of NaOAc Base and Resolving Agent Equivalents on Yield and Enantiomeric Purity of D-threo-Methylphenidate/Chiral Acid Salt Threo-methylphenidate hydrochloride (10.0 g, 0.037 mol) was suspended in methanol (36 g) and di-p-toluoyl-d-tartaric acid (D-TA) was charged (see Table 3 for charge quantities) followed by heating to 45° C. to provide a clear solution. To the formed solution NaOAc was added as a solid (see Table 3 for charge quantities). Deionized water was added to the mixture at about 45° C. to cause the reaction mixture to go clear and then upon continuous addition turn cloudy. The resulting slurry was cooled to 20° C. over 1 hour, aged for 2 hours, cooled to 0° C. and aged for 1 hour. The formed Dex-TA precipitate was filtered and washed sequentially with 20 ml of cold (0-5° C.) MeOH/water (2:1 w/w) mixture, 40 ml of deionized water and 40 ml acetone. The Dex-TA wet cake was dried at 50° C. in vacuum overnight.

TABLE 3

|  | D-TA | | NaOAc | | | Dex-TA | | |
| --- | --- | --- | --- | --- | --- | --- | --- | --- |
|  | Equiv | g | Equiv | g | Water g | g | Yield % | EE % |
| Ex 9 | 0.5 | 7.2 | 0.5 | 1.52 | 24 | 7.2 | 31.3 | 99.7 |
| Ex 10 | 0.5 | 7.2 | 1.0 | 3.04 | 22 | 8.7 | 37.8 | 99.6 |
| Ex 11 | 1.0 | 14.3 | 0.5 | 1.52 | 38 | 8.1 | 35.2 | 97.2 |
| Ex 12 | 1.0 | 14.3 | 1.0 | 3.04 | 15 | 9.6 | 41.7 | 99.6 |

The foregoing resolution processes utilizing an altogether different base, i.e. NaOAc, illustrates that it is the advantageous incorporation of a tertiary amine base which allows the beneficial use of less than equivalent amounts of base and/or chiral acid without significant sacrifice to ee and yield.

Example 13

Dexmethylphenidate Free Base and Hydrochloride Salt Formation

D-Threo-methylphenidate-di-p-toluoyl-D-tartrate (0.47 Kg, 0.758 mol, ee 98.9%) was charged to a suitable reactor followed by water (1.2 Kg) and isopropyl acetate (0.7 Kg). The formed slurry was cooled to about 15° C. and was treated with sodium hydroxide (25%, 0.3 Kg) at less than 25° C., followed by 30 minutes aging. The lower aqueous layer was separated and the organic layer was washed with process water (3×0.4 Kg)

The organic layer was dewatered by azeotropic distillation under vacuum and was concentrated in vacuum to give D-Threo-methylphenidate free base as an oil, which was used directly in hydrochloride salt formation. The solution of D-threo-methylphenidate free base in isopropanol (0.29 Kg) was charged to a jacketed vessel, cooled to 5-10° C. and treated with a solution of 37% HCl (78 g) in a mixture of isopropanol (40 g) and methanol (63 g) at less than 20° C. The formed slurry was cooled to 0 to 5° C., aged for 2 hours and filtered. The wet cake was washed with isopropanol (0.32 Kg total) in two portions and dried under vacuum at 45° C. for 16 hours to give Dexmethylphenidate hydrochloride (0.175 Kg, 0.649 mol, 86% yield) as a off-white solid; mp 206.4° C., ee 99.7%, $\alpha^{25}_D$ +83° (c 1 wt %, MeOH).

Example 14

Chiral Resolution of Racemic Threo-Methylphenidate to L-threo-Methylphenidate/Chiral Acid Salt Three-neck jacketed flask was charged with racemic threo-methylphenidate HCl (80.0 g, 0.297 mol) and methanol (280 g). The slurry was mixed for about 5 min and Di-O,O'-p-toluoyl-L-tartaric acid (74.3 g, 0.192 mol) was added to the slurry; the addition was completed by rinsing charge apparatus with methanol (8 g). N-Methylmorpholine (16.5 g, 0.163 mol) was charged and the reaction mixture was heated to 45° C. Water (180 g) was added to the reaction until a cloud point was achieved. The slurry was aged for 1 hour at 45° C., cooled to 20 to 25° C. and aged 1 hour. The formed precipitate was filtered and washed twice with cold methanol-water mixture (2×120 ml, 2:1 v/v). The wet cake (116 g) was dried at 50° C. in vacuum to yield L-threo-methylphenidate-di-p-toluoyl-L-tartrate (74.0 g, 40.3% of theory based on methylphenidate) as a white solid of 99.5% wt assay and 99.8% HPLC pure and 99.7% ee; mp 165.6-165.9° C.; $\alpha^{25}_D$ -120.10 (c 1 wt %, MeOH).

Accordingly, the inventive resolution process can be applied to resolve either enantiomer of threo-methylphenidate via diastereomeric salt formation with the corresponding chiral tartaric acid derivative.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

That which is claimed:

1. A process for isolating d-threo isomer of methylphenidate hydrochloride comprising the steps of:
   (i) resolving a mixture comprising
      racemic threo-methylphenidate hydrochloride;
      less than or equal to about 1.0 equivalent (based on the amount of racemic threo-methylphenidate hydrochloride) of chiral acid selected from one or more di-0-0'-aroyl-D-tartaric acids, about 0.4 to less than 1.0 equivalent (based on the amount of racemic threo-methylphenidate hydrochloride) of one or more tertiary amine bases, and
a solvent mixture comprising one or more lower alkanols and water, thereby forming a chiral acid-isomeric methylphenidate salt
(ii) basifying the chiral acid-isomeric methylphenidate salt to obtain isomeric methylphenidate free base and
(iii) converting the isomeric methylphenidate free base into isomeric methylphenidate hydrochloride having an enantiomeric excess of greater than about 90% and a yield of greater than about 35% based on racemic threo-methylphenidate hydrochloride.

2. A process according to claim 1, wherein said resolving step further comprises
(a) forming the resolution mixture at ambient temperature;
(b) heating the resolution mixture from step (a) to an effective temperature to dissolve the racemic threo-methylphenidate and chiral acid to form the chiral acid-isomeric methylphenidate salt and
(c) cooling the heated resolution mixture to a temperature and for a time effective to precipitate the chiral acid-isomeric methylphenidate salt.

3. A process according to claim 2, wherein
said heating step is performed at a temperature ranging from about 40 to 45° C. for a time period of about 15 minutes to 1 hour and
said cooling step is performed at a temperature of about 0 to 25° C. for a time period of about 2 to 6 hours.

4. A process according to claim 1, wherein the solvent mixture comprises lower alkanol and water in a weight ratio ranging from about 1.4:1 to 2.5:1.

5. A process according to claim 1, wherein the weight ratio for lower alkanol to racemic methylphenidate ranges from about 2.5:1 to 3.5:1.

6. A process according to claim 1, wherein the di-0,0'-aroyltartaric acid is selected from one or more of the group consisting of di-0,0'-p-toluoyl-D-tartaric acid, di-0,0'-m-toluoyl-D-tartaric acid and di-0,0'-benzoyl-D-tartaric acid.

7. A process for isolating l-threo isomer of methylphenidate hydrochloride comprising the steps of:
(i) resolving a mixture comprising
racemic threo-methylphenidate hydrochloride;
less than or equal to about 1.0 equivalent (based on the amount of racemic threo-methylphenidate hydrochloride) of chiral acid selected from one or more di-0,0'-L-aroyl tartaric acids,
about 0.4 to less than 1.0 equivalent (based on the amount of racemic threo-methylphenidate hydrochloride) of one or more tertiary amine bases, and
a solvent mixture comprising one or more lower alkanols and water, thereby forming a chiral acid-isomeric methylphenidate salt
(ii) basifying the chiral acid-isomeric methylphenidate salt to obtain isomeric methylphenidate free base and
(iii) converting the isomeric methylphenidate free base into isomeric methylphenidate hydrochloride having an enantiomeric excess of greater than about 90% and a yield of greater than about 35% based on racemic threo-methylphenidate hydrochloride.

8. A process according to claim 1, wherein the base is selected from one or more of the group consisting of triethylamine, diisopropylethylamine, N-methylmorpholine and sodium acetate.

9. A process according to claim 1, wherein the di-0,0'-aroyltartaric acid is di-0,0'-p-toluoyl-D-tartaric acid, the base is N-methylmorpholine and said process includes a single crystallization but does not include seeding.

10. A process according to claim 1, wherein the resolution mixture comprises a preformed salt of the base with di-0,0'-D-aroyltartaric acid.

11. A process according to claim 1, wherein the resolution mixture comprises greater than or equal to about 0.50 equivalents (based on the amount of racemic threo-methylphenidate) of chiral acid and greater than or equal to about 0.5 equivalents (based on the amount of racemic threo-methylphenidate) of base.

12. A process according to claim 11, wherein the resolution mixture comprises from about 0.55 to 0.75 equivalents (based on the amount of racemic threo-methylphenidate) of chiral acid and about 0.55 to 0.60 equivalents (based on the amount of racemic threo-methylphenidate) of base.

13. A process according to claim 1, wherein the lower alkanol within the solvent mixture is methanol.

14. A process according to claim 1, further comprising seeding the chiral acid-isomeric methylphenidate salt formed during resolution with an additional amount of chiral acid-isomeric methylphenidate, this additional amount having a higher enantiomeric excess than the chiral acid-isomeric methylphenidate formed in the resolution process, said seeding step performed prior to said salt basification step.

15. A process according to claim 1, further comprising purifying the chiral acid-isomeric methylphenidate salt formed during resolution prior to said salt basification step.

16. A process according to claim 1, wherein the salt basification step comprises
(i) converting the chiral acid-isomeric methylphenidate salt by basification with an alkali metal hydroxide solution into isomeric methylphenidate free base and
(ii) extracting the isomeric methylphenidate free base with an organic solvent.

17. A process according to claim 16, wherein the alkali metal hydroxide solution is an aqueous sodium hydroxide solution.

18. A process according to claim 16, wherein the organic solvent is an ester of acetic acid.

19. A process according to claim 16, wherein the organic solvent is selected from one or more of the group consisting of ethyl acetate and isopropyl acetate.

20. A process according to claim 1, wherein the converting step comprises combining the isomeric-methylphenidate free base produced in the salt basification step with a hydrochloride source in a conversion solvent in which the isomeric-methylphenidate hydrochloride crystallizes.

21. A process according to claim 20, wherein the hydrochloride source is selected from one or more of aqueous hydrochloric acid, gaseous hydrochloric acid, thionyl chloride and acetyl chloride.

22. A process according to claim 20, wherein the conversion solvent is selected from one or more of esters of acetic acid, lower alkanol and water.

23. A process according, to claim 20, wherein the conversion solvents are isopropyl alcohol and methanol.

24. A process according to claim 20, wherein the conversion solvent is a mixture of isopropyl alcohol and methanol, present in an isopropyl alcohol to methanol weight to weight ratio ranging from about 4:1 to 6:1.

25. A process for isolating d-threo-isomer of methylphenidate hydrochloride comprising the steps of:
(i) resolving a mixture comprising
racemic threo-methylphenidate hydrochloride;
less than or equal to about 1.0 equivalent (based on the amount of racemic threo-methylphenidate) of chiral acid selected from one or more of di-0,0'-p-toluoyl-D-tartaric acid, di-0,0'-m-toluoyl-D-tartaric acid, and di-0,0'-benzoyl-D-tartaric acid, about 0.4 to less than about 1.0 equivalent (based on the amount of racemic threo-methylphenidate) sodium acetate base, and a solvent mixture comprising one or more lower alkanols and water, thereby forming a chiral acid-isomeric methylphenidate salt (ii) basifying the chiral acid-isomeric methylphenidate salt to obtain isomeric methyl phenidate free base and (iii) converting the isomeric methylphenidate free base into isomeric methylphenidate hydrochloride having an enantiomeric excess of greater than about 90%, and a yield of greater than about 30% or more, bormp.

26. A process for resolving racemic threo-methylphenidate hydrochloride, said process comprising (a) providing a resolution mixture comprising
racemic threo-methylphenidate hydrochloride;
less than or equal to about 1.0 equivalent (based on the amount of racemic threo-methylphenidate) of one or more di-0,0'-D-aroyltartaric acids;
about 0.4 to less than about 1.0 equivalent (based on the amount of racemic threo-methylphenidate) of one or more tertiary amine bases, and
a solvent mixture comprising one or more lower alkanols and water, wherein said resolution results in chiral acid-isomeric methylphenidate salt having an enantiomeric excess of greater than or equal to about 90%.

27. A process according to claim 7, wherein the di-0,0'-L-aroyltartaric acid is selected from one or more of the group consisting of di-0,0'-p-toluoyl-L-tartaric acid, di-0,0'-m-toluoyl-L-tartaric acid and di-0,0'-benzoyl-L-tartaric acid.

28. A process as claimed in claim 1, said process comprising a single resolution step that includes chiral acid, present in an amount of about 1.0 equivalent (based on the amount of racemic threo-methylphenidate hydrochloride), and tertiary amine base, present in an amount of less than 0.75 equivalent (based on the amount of racemic threo-methylphenidate hydrochloride), wherein the said process includes a single crystallization but does not include seeding, the resulting isomeric methylphenidate hydrochloride having an enantiomeric excess of greater than about 99% and a yield of greater than about 40% based on racemic threo-methylphenidate hydrochloride.

* * * * *